(12) United States Patent
Koch et al.

(10) Patent No.: US 8,115,033 B2
(45) Date of Patent: Feb. 14, 2012

(54) 3-(4-HYDROXY-3-METHOXYPHENYL)-1-(4-HYDROXYPHENYL)-1-PROPANONE AND USE THEREOF AS AN ANTIMICROBIAL ACTIVE INGREDIENT

(75) Inventors: Oskar Koch, Göttingen (DE); Gerhard Schmaus, Höxter-Bosseborn (DE)

(73) Assignee: Symrise AG, Holzminden (DE)

( * ) Notice: Subject to any disclaimer, the term of this patent is extended or adjusted under 35 U.S.C. 154(b) by 0 days.

(21) Appl. No.: 12/670,509

(22) PCT Filed: Jul. 14, 2008

(86) PCT No.: PCT/EP2008/059179
§ 371 (c)(1),
(2), (4) Date: Jun. 16, 2010

(87) PCT Pub. No.: WO2009/013166
PCT Pub. Date: Jan. 29, 2009

(65) Prior Publication Data
US 2010/0254925 A1    Oct. 7, 2010

(30) Foreign Application Priority Data

Jul. 25, 2007    (DE) .......................... 10 2007 035 139

(51) Int. Cl.
C07C 45/00 (2006.01)
A61K 31/12 (2006.01)
A61K 8/18 (2006.01)

(52) U.S. Cl. ........ 568/312; 568/331; 514/685; 514/722; 424/65

(58) Field of Classification Search .................. 568/312, 568/331; 514/685, 722; 424/65
See application file for complete search history.

(56) References Cited

U.S. PATENT DOCUMENTS

| | | | |
|---|---|---|---|
| 3,043,802 A | 7/1962 | Thomas | |
| 3,295,974 A | 1/1967 | Erdmann | |
| 2008/0227867 A1* | 9/2008 | Ley et al. ...................... | 514/685 |

FOREIGN PATENT DOCUMENTS

| DE | 1099732 B | 2/1961 |
|---|---|---|
| DE | 1447016 A1 | 1/1969 |
| DE | 2256961 A1 | 5/1974 |
| DE | 3740186 A1 | 1/1989 |
| DE | 3938140 A1 | 8/1991 |
| DE | 4009347 A1 | 9/1991 |
| DE | 4204321 A1 | 8/1993 |
| DE | 4229707 A1 | 3/1994 |
| DE | 4229737 A1 | 3/1994 |
| DE | 4237081 A1 | 5/1994 |
| DE | 4309372 A1 | 9/1994 |
| DE | 4324219 A1 | 1/1995 |
| DE | 10356723 A1 | 6/2005 |
| JP | 20001549109 A | 6/2000 |

OTHER PUBLICATIONS

Forejtnikova et al. Chemoprotective and toxic potentials of synthetic and natural chalcones and dihydrochalcones in vitro. Toxicology, 2005, vol. 208, 81-93.*
Orjala et al., "Cytotoxic and Antibacterial Dihydrochalcones From *Piper aduncum*," Journal of Natural Products, vol. 57, No. 1. 1994, pp. 18-26, XP002497522.
Joshi et al., "Dihydrochalcones from *Piper longicaudatum*," Planta Medica, vol. 67, No. 2, Mar. 1, 2001, pp. 186-187.
Sato, T., et al., "Inhibition of Phenylalanine Ammonia-lyase by Flavonoids," Chem. Pharm. Bull., 31 (1) 149-155 (1983).
Muthusamy, A., et al., "Studies on Photoreactive Polyesters Containing α, β-Unsaturated Carbonyl Group in the Main Chain," High Performance Polymers, 18: 227-240, 2006.
Kaniappan, K., "Synthesis and Characterization of Photosensitive Phosphorus Based Polymers Containing α, β-Unsaturated Ketones in the Main Chain," Journal of Macromolecular Science, Part A: Pure and Applied Chemistry, 42: 1589-1602, 2005.
Zolfaghari, B., et al., "The Sapogenin Atroviolacegenin and Its Diglycoside Atroviolaceoside from *Allium atroviolaceum*," J. Nat. Prod. 2006, 69, 191-195.
Priyarega, S., "Synthesis and characterization of photosensitive polyesters by phase-transfer-catalyzed polycondensation," *Designed Monomers and Polymers*, vol. 6, No. 2, pp. 187-196 (2003).

* cited by examiner

*Primary Examiner* — Sikarl Witherspoon
(74) *Attorney, Agent, or Firm* — Connolly Bove Lodge & Hutz LLP

(57) ABSTRACT

Antimicrobially active 3-(4-hydroxy-3-methoxyphenyl)-1-(4-hydroxyphenyl)-1-propanone of the following formula 1 is described, as is a method for producing this compound and the use thereof as an antimicrobial active ingredient.

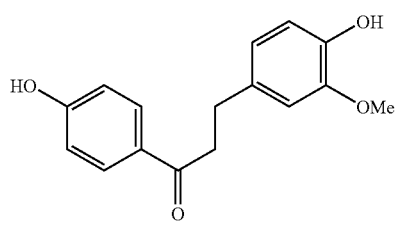

20 Claims, No Drawings

3-(4-HYDROXY-3-METHOXYPHENYL)-1-(4-HYDROXYPHENYL)-1-PROPANONE AND USE THEREOF AS AN ANTIMICROBIAL ACTIVE INGREDIENT

CROSS REFERENCE TO RELATED APPLICATIONS

This application is a National Phase filing under 35 U.S.C. §371 of PCT/EP2008/059179 filed Jul. 14, 2008, which claims priority to Application No. 102007035139.0 filed in Germany on Jul. 25, 2007 under 35 U.S.C. §119. The entire contents of each of the above-applications are fully incorporated herein by reference.

The present invention relates to the antimicrobially active compound 3-(4-hydroxy-3-methoxyphenyl)-1-(4-hydroxyphenyl)-1-propanone of the following formula 1, to a method for producing this compound and to the use thereof as an antimicrobial agent for treating body odor.

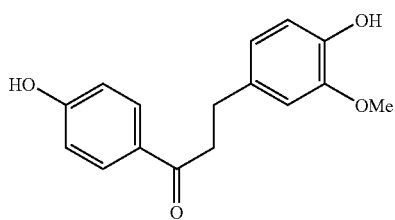

The compound is outstandingly suitable as an antimicrobial active ingredient for the cosmetic, in general for the dermatological treatment of microorganisms which cause body odor.

Human skin is colonized by numerous different bacteria. Most of these bacteria are non-pathogenic and of no relevance to the physiological condition of the skin and to its odor. Others, in contrast, can have a major influence on the healthy condition of the skin. Table 1 lists some microorganisms which have a strong influence on human skin.

TABLE 1

| Microorganisms: | |
|---|---|
| Staphylococcus epidermidis | Underarm odor; body odor in general |
| Corynebacterium xerosis | Underarm odor |
| Brevibacterium epidermidis | Underarm odor; foot odor |
| Escherichia coli | Wound infections |
| Pseudomonas aeruginosa | Wound infections |
| Malassezia furfur (syn. Pityrosporum ovale) | Dandruff |
| Candida albicans | Candidiasis in general |
| Trichophyton mentagrophytes | Skin and nail mycoses |
| Trichophyton rubrum | Skin and nail mycoses |
| Epidermophyton floccosum | Skin and nail mycoses |

Bacterial degradation of endogenous substances present in perspiration, such as for example unsaturated fatty acids, gives rise from precursors, which to a greater or lesser extent have a slight odor, to unpleasant smelling decomposition products which can have a major impact on physical well-being. Formation of the substances responsible for body odor is prevented in cosmetic applications either by using products which suppress the formation of sweat ("antiperspirants") or by using substances which inhibit the growth of human skin bacteria responsible for odor formation ("deodorants"). Species of bacteria such as *Staphylococcus epidermidis, Corynebacterium xerosis* and *Brevibacterium epidermidis* are largely responsible for the formation of underarm and foot odor, or body odor in general. There is accordingly a constant need in the cosmetics industry for new agents for treating these microorganisms and others which cause body odor (including underarm and foot odor).

For the purposes of the present document, "treatment" should be taken to mean exerting any kind influence on the microorganisms in question, in which multiplication of these microorganisms is inhibited and/or the microorganisms are killed.

In seeking out such antimicrobially active agents, it must be borne in mind that the substances used in cosmetic and/or pharmaceutical products must furthermore
- be toxicologically safe,
- exhibit good skin compatibility,
- be stable (in particular in conventional cosmetic and/or pharmaceutical formulations),
- preferably have a slight odor or be (largely) odorless,
- preferably be colorless and cause no discoloration, and
- be inexpensive to produce (i.e. using standard methods and/or starting from standard precursors).

The search for suitable (active) substances which exhibit one or more of the stated characteristics to a sufficient extent is complicated for a person skilled in the art by the fact that there is no clear dependency between the chemical structure of a substance, on the one hand, and its biological activity towards specific microorganisms (microbes) and their stability, on the other hand. Moreover, there is no predictable connection between antimicrobial action, toxicological safety, skin compatibility and/or stability.

It was accordingly the object of the present invention to provide an antimicrobial active ingredient which is active in particular against microorganisms such as *Corynebacterium xerosis, Staphylococcus epidermidis* and *Brevibacterium epidermidis*, which cause body odor and foot odor, and which in so doing preferably also satisfies one or more of the above-stated secondary conditions.

It has surprisingly now been found that the novel compound according to the invention of the formula 1, namely 3-(4-hydroxy-3-methoxyphenyl)-1-(4-hydroxyphenyl)-1-propanone, has excellent antimicrobial properties and in particular is active against the stated microorganisms. Further investigations into its chemical properties revealed that the compound is distinguished by high stability, in particular by elevated temperature stability and by high stability over a wide range of pH values, as a consequence of which it is ideally suitable for use in the most varied range of cosmetic products (cosmetic formulations), medical devices and pharmaceutical products. In addition, in pure form, the compound according to the invention of the formula 1 is a white solid which forms a colorless solution in (cosmetic and/or pharmaceutical) carriers; furthermore, no discoloration was observed after incorporation of the compound according to the invention of the formula 1 in cosmetic products, in medical devices and in pharmaceutical preparations.

A method for producing the compound of the formula 1 and the use thereof as an antimicrobial active ingredient in cosmetic products, in medical devices and in pharmaceutical preparations are likewise described here for the first time.

The compound of the formula 1 has a strong antimicrobial action towards odor-forming microorganisms on human skin and may thus ideally be used as a deodorant as an alternative or supplement to known antimicrobial active ingredients (such as for example farnesol) in cosmetic products, in medical devices, in pharmaceutical products and the like.

The usage concentration of the compound according to the invention of the formula 1 in a cosmetic final product is here preferably in the range between 0.001 to 10 wt. %, preferably in the range between 0.005 and 5 wt. % and particularly preferably in the range between 0.01 and 1.0 wt. %, in each case relative to the total mass of the cosmetic product, the medical device or the pharmaceutical agent.

In a preferred method for cosmetic and/or therapeutic treatment of microorganisms which cause body odor, an antimicrobially active amount of the compound according to the invention of the formula 1 is applied topically onto the human or animal body, such that growth of the microorganism(s) which are possibly present is inhibited and/or they are killed.

The substance according to the invention of the formula 1 may also be used as a constituent of fragrance compositions (odoriferous substance compositions) and, for example, impart an antimicrobial action to a perfumed finished product. A particularly preferred fragrance composition comprises (a) an organoleptically active amount of a fragrance, (b) an antimicrobially active amount of the compound of the formula 1 and (c) optionally one or more carriers and/or additives. Since the proportion of perfume in a cosmetic finished product is frequently of the order of approx. 1 wt. %, a perfume which contains the compound according to the invention of the formula 1 will preferably consist to an extent of approx. 5-50 wt. % of the compound of the formula 1. It has proved particularly advantageous that the compound of the formula 1 has a weak intrinsic odor reminiscent of vanilla pods; this characteristic makes it ideally suitable for use as a deodorizing active ingredient in a fragrance composition.

The invention also relates to antimicrobial compositions which, in addition to (a) an antimicrobially active amount of the compound according to the invention of the formula 1, also comprise (b) a carrier substance compatible with component (a).

The compound according to the invention of the formula 1 may be obtained by a production method which comprises the following step:

(b) reduction, preferably hydrogenation, of 3-(4-hydroxy-3-methoxyphenyl)-1-(4-hydroxyphenyl)-2-propen-1-one.

The compound according to the invention of the formula 1 may preferably be obtained by a production method which comprises the following steps:

(a) reaction (aldol condensation) of p-hydroxyacetophenone with vanillin, (b) reduction, preferably hydrogenation, of the reaction product obtained in step (a).

The unsaturated ketone 3-(4-hydroxy-3-methoxyphenyl)-1-(4-hydroxyphenyl)-2-propen-1-one of reaction step a) is known from the literature, for example from DE 1 099 732 (for the production of polycarbonates), DE 1 447 016 (for the production of photosensitive materials), DE 2 256 961 (for the production of epoxy resins), Chem. Pharm. Bull. 1983, 31(1), 149-155 (investigation of the inhibition of phenylalanine ammonia-lyase), Designed Monomers and Polymers (2003), 6(2), 187-196, High Performance Polymers (2006), 18(2), 227-240 and J. of Macromolecular Science, Part A: Pure and Applied Chemistry (2005), A42(12), 1589-1602 (in each case for the production of polymers), Journal of Natural Products (2006), 69(2), 191-195 (detection in *Allium atroviolaceum*).

The production method preferred according to the invention may be illustrated by the following scheme:

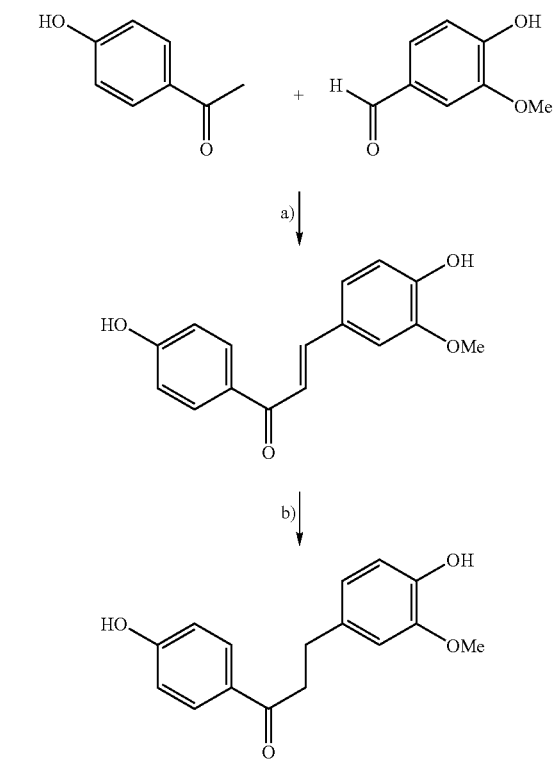

Further aspects of the present invention are disclosed by the attached claims and the following Examples. Unless otherwise stated, all stated values relate to weight.

In various cases, it may also be advantageous to add to the cosmetic and pharmaceutical, preferably dermatological, preparations according to the invention one, two, three, four or further substances which are primarily used to inhibit growth of undesired microorganisms on or in animal organisms. Further active ingredients which may be mentioned in this respect in addition to the large group of conventional antibiotics are those products of particular relevance to cosmetics such as Triclosan® (5-chloro-2-(2,4-dichlorophenoxy)phenol), climbazole, zinc pyrithione, ichthyol, Octopirox (1-hydroxy-4-methyl-6-(2,4,4-trimethylpentyl)-2 (1H)-pyridone, 2-aminoethanol), chitosan, farnesol, hexoxyglycerin, octoxyglycerin (=ethylhexylglycerin, 3-(2-ethylhexyloxy-1,2-propanediol), for example Sensiva® SC 50 from Schülke & Mayr), glycerol monolaurate, arylalkyl alcohols such as for example phenylethyl alcohol, 3-phenyl-1-propanol, veticol (4-methyl-4-phenyl-2-pentanol) or muguet alcohol (2,2-dimethyl-3-phenylpropanol), polyglycerol esters, such as for example polyglyceryl 3-caprylate, aliphatic 1,2-diols such as for example 1,2-pentanediol, 1,2-hexanediol, 1,2-octanediol, and 1,2-decanediol and alkyl-branched carboxylic acids such as 2-butyloctanoic acid, 2-butyldecanoic acid, 2-hexyloctanoic acid and 2-hexyldecanoic acid or combinations of the stated substances, which are used inter alia against underarm odor, foot odor or dandruff.

The cosmetic and pharmaceutical, preferably dermatological, preparations according to the invention may also furthermore contain one, two, three, four or more antiperspirant active ingredients (antiperspirants) and/or odor absorbers.

Antiperspirant active ingredients which may preferably be used are aluminum salts such as aluminum chloride, aluminum chlorohydrate, nitrate, sulfate, acetate etc. In addition, however, the use of zinc, magnesium and zirconium compounds may also be advantageous. It is primarily aluminum salts and, to a somewhat lesser extent, aluminum/zirconium salt combinations which have proved effective for use in cosmetic and pharmaceutical, preferably dermatological, antiperspirants. Also worthy of mention are the partially neutralized and thus more skin compatible, but not quite so active aluminum hydroxychlorides. In addition to aluminum salts, further substances are also feasible, such as for example a) protein-precipitating substances such as inter alia formaldehyde, glutaraldehyde, natural and synthetic tannins together with trichloroacetic acid, which bring about superficial closure of the sweat glands, b) local anesthetics (inter alia diluted solutions of for example lidocaine, prilocaine or mixtures of such substances), which switch off sympathetic supply of the sweat glands by blockading the peripheral nerve pathways, c) zeolites of the X-, A- or Y-type, which, in addition to reducing sweat secretion, also function as adsorbents for bad odors and d) botulinum toxin (toxin of the bacterium *Clostridium botulinum*), which is also used in the case of hyperhydrosis, i.e. pathologically elevated sweat secretion, and whose action is based on irreversible blocking of the release of the transmitter substance acetylcholine which is of relevance in sweat secretion.

Odor absorbers are for example the phyllosilicates described in DE 40 09 347, of these in particular montmorillonite, kaolinite, nontronite, saponite, hectorite, bentonite, smectite, furthermore for example zinc salts of ricinoleic acid. These also include bactericidal or bacteriostatic deodorizing substances, such as for example hexachlorophene, 2,4,4'-trichloro-2'-hydroxydiphenyl ether (Irgasan), 1,6-di-(4-chlorophenyldiguanidino)hexane (chlorhexidine), 3,4,4'-trichlorocarbanilide, and the active agents described in published patent applications DE-37 40 186, DE-39 38 140, DE-42 04 321, DE-42 29 707, DE-42 29 737, DE-42 37 081, DE-43 09 372, DE-43 24 219, and contain cationically active substances, such as for example quaternary ammonium salts and odor absorbers, such as for example Grillocin® (combination of zinc ricinoleate and various additives) or triethyl citrate, optionally in combination with ion-exchange resins.

Cosmetic and pharmaceutical, preferably dermatological, preparations according to the invention may also in many cases advantageously contain one, two, three, four or more preservatives. Preservatives which are preferably selected are those such as benzoic acid and the esters and salts thereof, 4-hydroxybenzoic acid and the esters ("parabens") and salts thereof, propionic acid and the esters and salts thereof, salicylic acid, and the esters and salts thereof, 2,4-hexadienoic acid (sorbic acid) and the esters and salts thereof, formaldehyde and paraformaldehyde, 2-hydroxybiphenyl ether and the salts thereof, 2-zinc sulfidopyridine N-oxide, inorganic sulfites and bisulfites, sodium iodate, chlorobutanol, 4-ethylmercury(II) 5-amino-1,3-bis(2-hydroxybenzoic acid), the salts and esters thereof, dehydracetic acid, formic acid, 1,6-bis(4-amidino-2-bromophenoxy)-n-hexane and the salts thereof, the sodium salt of ethylmercury(II) thiosalicylic acid, phenylmercury and the salts thereof, 10-undecenoic acid and the salts thereof, 5-amino-1,3-bis(2-ethylhexyl)-5-methylhexahydropyrimidine, 5-bromo-5-nitro-1,3-dioxane, 2-bromo-2-nitro-1,3-propanediol, 2,4-dichlorobenzyl alcohol, N-(4-chlorophenyl)-N'-(3,4-dichlorophenyl)-urea, 4-chloro-m-cresol, 2,4,4'-trichloro-2'-hydroxy-diphenyl ether, 4-chloro-3,5-dimethylphenol, 1,1'-methylene-bis(3-(1-hydroxymethyl-2,4-dioximidazolidin-5-yl)urea), poly (hexamethylene biguanide) hydrochloride, 2-phenoxyethanol, hexamethylene tetramine, 1-(3-chloroallyl)-3,5,7-triaza-1-azonia adamantane chloride, 1-(4-chlorophenoxy)1(1H-imidazol-1-yl)-3,3-dimethyl-2-butanone, 1,3-bis (hydroxymethyl)-5,5-dimethyl-2,4-imidazolidindione, benzyl alcohol, Octopirox, 1,2-dibromo-2,4-dicyanobutane, 2,2'-methylene-bis(6-bromo-4-chlorophenol), bromochlorophene, mixture of 5-chloro-2-methyl-3(2H)-isothiazolinone and 2-methyl-3(2H)isothiazolinone with magnesium chloride and magnesium nitrate, 2-benzyl-4-chlorophenol, 2-chloroacetamide, chlorhexidine, chlorhexidine acetate, chlorhexidine gluconate, chlorhexidine hydrochloride, 1-phenoxy-propan-2-ol, N-alkyl($C_{12}$-$C_{22}$)trimethylammonium bromide and chloride, 4,4-dimethyl-1,3-oxazolidine, N-hydroxymethyl-N-(1,3-di(hydroxymethyl)-2,5-dioxoimidazolidin-4-yl)-N'-hydroxymethylurea, 1,6-bis(4-amidinophenoxy)-n-hexane and the salts thereof, glutaraldehyde, 5-ethyl-1-aza-3,7-dioxabicyclo(3.3.0)octane, 3-(4-chlorophenoxy)-1,2-propanediol, Hyamine, alkyl-($C_8$-$C_{18}$)-dimethylbenzylammonium chloride, alkyl-($C_8$-$C_{18}$)-dimethylbenzylammonium bromide, alkyl-($C_8$-$C_{18}$)-dimethylbenzylammonium saccharinate, benzylhemiformal, 3-iodo-2-propynyl butylcarbamate, sodium hydroxymethylaminoacetate or sodium hydroxymethylaminoacetate.

The claims and Examples below illustrate the invention or individual aspects thereof in greater detail. Unless otherwise stated, all stated values relate to weight.

EXAMPLE 1

Synthesis of 3-(4-hydroxy-3-methoxyphenyl)-1-(4-hydroxyphenyl)-1-propanone of the formula 1

(a) Reaction of p-hydroxyacetophenone with Vanillin:

20 g of potassium hydroxide are initially introduced into 100 g of diethylene glycol diethyl ether, heated to 120° C. with stirring and combined with a mixture of 14 g of p-hydroxyacetophenone and 15 g of vanillin within 1 h. Once addition is complete, stirring is continued for a further 20 min, the mixture hydrolyzed and adjusted to pH 6-7. Once the phases have separated, the solvent is removed and 25 g of 3-(4-hydroxy-3-methoxyphenyl)-1-(4-hydroxyphenyl)-2-propen-1-one are obtained, yield: 93% of theoretical.

(b) Hydrogenation of the Reaction Product Obtained in Step (a):

10 g of 3-(4-hydroxy-3-methoxyphenyl)-1-(4-hydroxyphenyl)-2-propen-1-one are dissolved in 100 g of tetrahydrofuran, combined with 0.2 g of Pd on activated carbon (Pd content: 5 wt. %, water content approx. 50 wt. %, in each case relative to the total mass of the catalyst) and hydrogenated at standard pressure and room temperature (approx. 20° C.) After removal of the catalyst and the solvent, 9 g of 3-(4-hydroxy-3-methoxyphenyl)-1-(4-hydroxyphenyl)-propan-1-one are obtained. Yield: 89% of theoretical Spectroscopic data for 1-propanone, 3-(4-hydroxy-3-methoxyphenyl)-1-(4-hydroxyphenyl)-(formula 1):

$^{13}$C-NMR (CDCl$_3$; 75.5 MHz): δ (ppm)=197.42(s), 161.85(s), 147.24(s), 144.44(s), 132.03(s), 130.37(d), 130.37 (d), 128.18(s), 120.27(d), 115.11(d), 115.07(d), 115.07(d), 112.53(d), 55.42(q), 39.30(t), 29.42(t);

MS: m/z (%)=M$^+$ ion 272(82), 151(24), 137(77), 121(100), 93(19), 65(22).

EXAMPLE 2

Investigations into the Antimicrobial Action of 3-(4-hydroxy-3-methoxyphenyl)-1-(4-hydroxyphenyl)-1-propanone of the Formula 1

EXAMPLE 2.1

Method

The recognition that 3-(4-hydroxy-3-methoxyphenyl)-1-(4-hydroxyphenyl)-1-propanone of the formula 1 is very particularly suitable for combating microorganisms which are responsible for body odor is based on series of investigations relating to the particularly relevant microorganisms *Staphylococcus epidermidis*, *Corynebacterium xerosis* and *Brevibacterium epidermidis*.

The antimicrobial action of 3-(4-hydroxy-3-methoxyphenyl)-1-(4-hydroxyphenyl)-1-propanone is here detected with the assistance of a turbidimetric measurement method. Turbidity measurement is used to establish growth curves for the particular microorganism in the presence and absence of an antimicrobial active ingredient. A possible inhibitory action of the test substance used is identified from the profile of the growth curves. Solutions with saline or DMSO for 100% growth are prepared as a negative control.

The active substances to be investigated are first diluted in DMSO in reaction vessels. Dilution is carried out in accordance with the concentration range to be tested and corresponds in each case to 100 times the concentration of the subsequent final concentration in the test. Testing is usually begun with a final concentration of 2000 ppm in the test. Growth curves at final concentrations of 1000 ppm, 500 ppm, 250 ppm, 125 ppm, 64 ppm, 32 ppm, 16 ppm and 8 ppm are subsequently determined.

The bacterial cultures are then incubated in the presence of the various final concentrations of antimicrobial active ingredient for 16 h (incubation temperature: 37° C.). The absorption values (wavelength 620 nm; measurement interval: 20 minutes) obtained over the 16 hour period of turbidimetric measurement are recorded and exported into the spreadsheet program MS Excel. Means from in each case three parallel batches are calculated and used as the basis for establishing growth curves. The curves of the individual test sample concentrations are compared with those for the negative controls and the MIC value (minimum inhibitory concentration) is determined. The MIC value is the concentration at which no further growth is observable by turbidimetry.

EXAMPLE 2.2

MIC Value of 3-(4-hydroxy-3-methoxyphenyl)-1-(4-hydroxyphenyl)-1-propanone

MIC values of the compound according to the invention, 1-propanone, 3-(4-hydroxy-3-methoxyphenyl)-1-(4-hydroxyphenyl)- were determined in accordance with the general test conditions described in 2.1. Complete inhibition of growth for *Corynebacterium xerosis* (DSM 20743) was determined at a usage concentration of just 500 ppm, so demonstrating this compound's good antimicrobial activity. It likewise proved possible to establish inhibition of the growth of further Gram positive bacteria which cause body odor such as *Staphylococcus epidermidis* (ATCC 12228), *Brevibacterium epidermidis* (ATCC 35514) by 3-(4-hydroxy-3-methoxyphenyl)-1-(4-hydroxyphenyl)-1-propanone in a concentration of below 0.1 wt. % using the test method described in 2.1.

It proved possible to confirm the antimicrobial activity of 3-(4-hydroxy-3-methoxyphenyl)-1-(4-hydroxyphenyl)-1-propanone towards microorganisms which cause body odor such as *Corynebacterium xerosis* (DSM 20743), *Staphylococcus epidermidis* (ATCC 12228) and *Brevibacterium epidermidis* (ATCC 35514) both with the assistance of further in vitro methods such as the quantitative suspension test and by means of in vivo sniffing tests on groups of human test subjects suffering from severe body odor.

The antimicrobially active 3-(4-hydroxy-3-methoxyphenyl)-1-(4-hydroxyphenyl)-1-propanone of the formula 1, in particular insofar as it is used against microorganisms which cause body odor, is generally applied topically in the form of solutions, creams, lotions, gels, sprays, or the like. For other purposes, administration may conveniently proceed orally (tablets, capsules, powders, drops), intravenously, intraocularly, intraperitoneally or intramuscularly or in the form of an impregnated dressing.

The concentration of the antimicrobially active compound of the formula 1 in the (topically) administered formulations is preferably in the range from 0.001%-10 wt. %, preferably in the range from 0.005-5 wt. % and particularly preferably in the range from 0.01-1 wt. %. The antimicrobial active ingredient may here be used (a) preventively or (b) when required.

The concentration of the active ingredient which is to be applied for example daily varies and depends on the physiological condition of the test subjects and on specific individual parameters such as age or body weight. 3-(4-Hydroxy-3-methoxyphenyl)-1-(4-hydroxyphenyl)-1-propanone may be used not only alone but also in combination with further antimicrobial active substances.

FORMULATION EXAMPLES

All formulation examples F1-F5 were formulated twice using the following two perfumes separately (DPG=dipropylene glycol):

Perfume Type "Rose"

| Fragrance material | Parts by weight |
| --- | --- |
| Acetophenone, 10% in DPG | 10 |
| n-Undecanal | 5 |
| Aldehyde C14, so-called | 15 |
| Allyl amylglycolate, 10% in DPG | 20 |
| Amyl salicylate | 25 |
| Benzyl acetate | 60 |
| Citronellol | 80 |
| d-Limonene | 50 |
| Decenol trans-9 | 15 |
| Dihydromyrcenol | 50 |
| Dimethyl benzyl carbinyl acetate | 30 |
| Diphenyl oxide | 5 |
| Eucalyptol | 10 |
| Geraniol | 40 |
| Nerol | 20 |
| Geranium oil | 15 |
| Hexenol cis-3, 10% in DPG | 5 |
| Hexenyl salicylate, cis-3 | 20 |
| Indole, 10% in DPG | 10 |
| Alpha-Ionone | 15 |
| Beta-Ionone | 5 |
| Lilial ® (2-Methyl-3-(4-tert-butyl-phenyl)propanal) | 60 |
| Linalool | 40 |
| Methylphenyl acetate | 10 |
| Phenylethyl alcohol | 225 |
| Styrolyl acetate | 20 |
| Terpineol | 30 |
| Tetrahydrolinalool | 50 |

-continued

| Fragrance material | Parts by weight |
|---|---|
| Tonalide ® (musk) | 50 |
| Cinnamic alcohol | 10 |
| TOTAL: | 1000 |

Perfume Type "White Blossom"

| Fragrance material | Parts by weight |
|---|---|
| Benzyl acetate | 60 |
| Citronellyl acetate | 60 |
| Cyclamenaldehyde (2-Methyl-3-(4-isopropylphenyl)propanal | 20 |
| Dipropylene glycol | 60 |
| Ethyllinalool | 40 |
| Florol (2-isobutyl-4-methyltetrahydro-2H-pyran-4-ol) | 30 |
| Globanone ® [(E/Z)-8-cyclohexadecen-1-one] | 160 |
| Hedione ® (methyl dihydrojasmonate) | 130 |
| Hexenyl salicylate, cis-3 | 10 |
| Vertocitral (2,4-dimethyl-3-cyclohexencarboxaldehyde) | 5 |
| Hydratropaldehyde, 10% in DPG | 5 |
| Isodamascone (1-(2,4,4-trimethyl-2-cyclohexen-1-yl)-2-buten-1-one), 10% in DPG | 5 |
| Isomuscone (cyclohexadecanone) | 85 |
| Jacinthaflor (2-methyl-4-phenyl-1,3-dioxolane) | 10 |
| Cis-Jasmone, 10% in DPG | 20 |
| Linalool | 50 |
| Linalyl acetate | 30 |
| Methyl benzoate, 10% in DPG | 25 |
| Galaxolide ® (musk) | 50 |
| Nerol | 20 |
| Phenylpropyl aldehyde | 5 |
| 2-Phenylethyl alcohol | 85 |
| Tetrahydrogeraniol | 15 |
| 2,2-Dimethyl-3-cyclohexyl-1-propanol | 20 |
| TOTAL: | 1000 |

EXAMPLE F1

Aerosol Spray

| Component | Wt. % |
|---|---|
| Aluminum Chlorohydrate | 30.00 |
| 3-(4-Hydroxy-3-methoxyphenyl)-1-(4-hydroxyphenyl)-1-propanone of formula 1 | 0.10 |
| Persea Gratissima Oil | 0.10 |
| Octyldodecanol | 1.00 |
| Dimethicone | 3.00 |
| Cyclomethicone | ad 100 |
| Perfume | 7.00 |
| Magnesium Aluminum Silicate | 0.10 |
| Disteardimonium Hectorite | 4.00 |
| Tocopheryl Acetate | 0.10 |
| Butyloctanoic acid | 0.25 |

15 Parts of the mixture obtained by mixing together the listed components were filled with 85 parts by weight of a propane-butane mixture (propane:butane=2:7 (w/w)) into an aerosol container.

EXAMPLE F2

Roll-On (Macro-Emulsion)

| Component | Wt. % |
|---|---|
| 3-(4-Hydroxy-3-methoxyphenyl)-1-(4-hydroxyphenyl)-1-propanone of formula 1 | 0.125 |
| Trisodium EDTA | 1.50 |
| Steareth-21 | 1.50 |
| Steareth-2 | 2.50 |
| PPG-15 Stearyl Ether | 3.00 |
| Aluminum Chlorohydrate | 20.00 |
| Perfume | 1.00 |
| Water (Aqua) | ad 100 |

EXAMPLE F3

Roll-On (Micro-Emulsion)

| Component | Wt. % |
|---|---|
| 3-(4-Hydroxy-3-methoxyphenyl)-1-(4-hydroxyphenyl)-1-propanone of formula 1 | 0.50 |
| Aluminum Chlorohydrate | 20.00 |
| 1,3-Butylene Glycol | 3.00 |
| Dicaprylyl Ether | 3.00 |
| Isoceteth-20 | 5.00 |
| Glyceryl Isostearate | 2.50 |
| PEG-150 Distearate | 1.00 |
| Perfume | 0.80 |
| Water (Aqua) | ad 100 |

EXAMPLE F4

Deodorant Stick

| Component | Wt. % |
|---|---|
| 3-(4-Hydroxy-3-methoxyphenyl)-1-(4-hydroxyphenyl)-1-propanone of formula 1 | 0.25 |
| Stearic Acid | 6.50 |
| 1,2-Propylene Glycol | 20.00 |
| PEG-8 | 20.00 |
| Ethylhexylglycerin | 0.50 |
| Persea Gratissima Oil | 0.10 |
| Octyldodecanol | 0.10 |
| Perfume | 1.00 |
| Water (Aqua) | Ad 100 |
| Butyloctanoic Acid | 0.50 |
| Distarch Phosphate | 0.40 |

EXAMPLE F5

Antiperspirant Cream Deodorant for Sensitive Skin

| Component | Wt. % |
|---|---|
| 3-(4-Hydroxy-3-methoxyphenyl)-1-(4-hydroxyphenyl)-1-propanone of formula 1 | 0.20 |
| Paraffinum Liquidum | 4.50 |
| Glyceryl Stearate | 5.00 |
| Water (Aqua) | ad 100 |
| Cetyl Alcohol | 5.00 |
| PEG-40 Stearate | 2.50 |
| Trisodium EDTA | 1.50 |
| Persea Gratissima Oil | 0.10 |
| C12-15 Alkyl Benzoate | 0.50 |
| Aluminum Chlorohydrate | 30.00 |
| C13-16 Isoparaffin | 4.50 |
| Isohexadecane | 4.50 |
| Caprylyl Glycol (1,2-octanediol) | 0.30 |
| Perfume | 0.50 |

The invention claimed is:

1. A compound of the formula

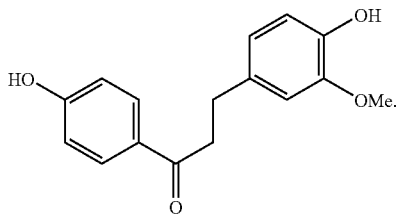

2. A method for killing bacteria in perspiration comprising contacting the bacteria with the compound of claim 1.

3. A method for producing the compound of claim 1, comprising reducing 3-(4-hydroxy-3-methoxyphenyl)-1-(4-hydroxyphenyl)-2-propen-1-one to afford the compound of claim 1.

4. A method for making an antimicrobially active cosmetic formulation, an antimicrobially active medical device, or an antimicrobially active pharmaceutical formulation comprising adding an antimicrobially active amount of a compound of claim 1 to a cosmetic formulation, a medical device, or a pharmaceutical formulation.

5. A method for the cosmetic and/or therapeutic treatment of body odor comprising the topical administration of an antimicrobially active amount of the compound according to claim 1 onto a human or animal body.

6. A composition comprising:
   (a) an antimicrobially active amount of a compound of the formula

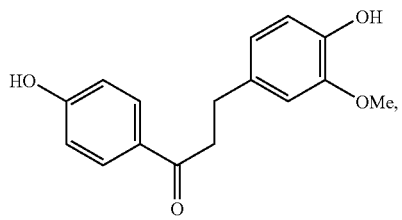

and
   (b) a carrier substance compatible with component (a).

7. The composition as claimed in claim 6, wherein the composition is a cosmetic formulation, a medical device, or a pharmaceutical formulation.

8. A fragrance composition comprising:
   (a) an organoleptically active amount of a fragrance;
   (b) an antimicrobially active amount of the compound according to claim 1; and
   (c) optionally one or more carriers and/or additives.

9. The method of claim 5, wherein the body odor is underarm odor.

10. The method of claim 5, wherein the body odor is foot odor.

11. The method of claim 3, wherein the reduction is a hydrogenation.

12. A method for producing the compound as claimed in claim 1, comprising:
   (a) reacting by aldol condensation p-hydroxyacetophenone with vanillin; and
   (b) reducing the reaction product obtained in step (a) to afford the compound of claim 1.

13. The method of claim 12, wherein the reduction is a hydrogenation.

14. The composition of claim 6 comprising from 0.001 to 10 wt % of the compound of component (a).

15. The composition of claim 6 comprising from 0.005 to 5 wt % of the compound of component (a).

16. The composition of claim 6 comprising from 0.01 to 1.0 wt % of the compound of component (a).

17. The method according to claim 2, wherein the bacteria is at least one of: *Corynebacterium xerosis, Staphylococcus epidermidis,* or *Brevibacterium epidermidis*.

18. The fragrance composition according to claim 8, wherein the fragrance composition comprises approximately 5-50 wt. % of the compound of Formula (I).

19. The composition according to claim 6, wherein the composition is in the form of a solution, cream, lotion, gel, spray, tablet, capsule, powder, or drop.

20. The composition according to claim 6, further comprising at least one of:
   (a) a substance which is primarily used to inhibit growth of undesired microorganisms on or in animal organisms;
   (b) an antiperspirant active ingredient;
   (c) an odor absorber; or
   (d) a preservative.

* * * * *